(12) United States Patent
Freedgood (10) Patent No.: US 7,888,656 B2
(45) Date of Patent: Feb. 15, 2011

(54) UV SANITIZER FOR TETHERED AND UNTETHERED MOUTHGUARDS

(75) Inventor: Marc Freedgood, Sherborn, MA (US)

(73) Assignee: Breakaway Products, LLC, East Walpole, MA (US)

( * ) Notice: Subject to any disclaimer, the term of this patent is extended or adjusted under 35 U.S.C. 154(b) by 427 days.

(21) Appl. No.: 12/137,656

(22) Filed: Jun. 12, 2008

(65) Prior Publication Data

US 2009/0311149 A1 Dec. 17, 2009

(51) Int. Cl.
A61L 2/10 (2006.01)
G21K 5/02 (2006.01)

(52) U.S. Cl. .............. 250/455.11; 250/453.11; 250/454.11; 250/504 R; 250/504 H; 422/20; 422/24

(58) Field of Classification Search ............ 250/453.11, 250/454.11, 455.11, 493.1, 494.1, 504 R, 250/504 H; 422/1, 20, 21, 22, 24, 27, 186, 422/186.3

See application file for complete search history.

(56) References Cited

U.S. PATENT DOCUMENTS

| | | | |
|---|---|---|---|
| 3,955,922 A * | 5/1976 | Moulthrop ............. 422/300 |
| 4,977,905 A * | 12/1990 | Kittelsen et al. ............ 128/861 |
| 5,968,036 A | 10/1999 | Goodman |
| 6,397,848 B1 | 6/2002 | Kagekata |
| 6,461,568 B1 | 10/2002 | Eckhardt |
| D537,987 S | 3/2007 | Manzo |
| 7,213,603 B2 * | 5/2007 | Pinsky ................. 132/310 |
| 2002/0146343 A1 | 10/2002 | Jenkins |
| 2004/0089815 A1 | 5/2004 | Woo |
| 2004/0118427 A1 * | 6/2004 | Palfy et al. ............... 134/1 |
| 2006/0065277 A1 | 3/2006 | Jacobs |
| 2006/0117472 A1 | 6/2006 | Gollarza |
| 2006/0242788 A1 * | 11/2006 | Day ..................... 15/363 |
| 2007/0031776 A1 | 2/2007 | Sakaguchi |

* cited by examiner

*Primary Examiner*—Jack I Berman
*Assistant Examiner*—Nicole Ippolito Rausch
(74) *Attorney, Agent, or Firm*—Albert Peter Durigon (57) ABSTRACT

A portable, battery-powered UV sanitizer kills germs and bacteria on the mouthpieces of tethered mouthguards of a wide variety of tether sizes and configurations and on the mouthpieces of untethered mouthguards. It doubles as a protective case when not in antimicrobial use. It includes a dishwasher safe detachable tray. It may be used with other dental appliances.

19 Claims, 12 Drawing Sheets fig.1 fig.2 fig.3 fig.4 fig.5 fig.6 fig.7 fig.8 fig.9 fig.10 fig.11 fig.12 fig.13 fig.14

UV SANITIZER FOR TETHERED AND UNTETHERED MOUTHGUARDS

FIELD OF THE INVENTION

This invention is drawn to the field of sanitizing apparatus, and more particularly, to portable UV sanitizers for tethered and untethered mouthguards.

BACKGROUND OF THE INVENTION

Mouthguards are dental appliances worn in the mouth of athletes to help protect their teeth against sports injuries. Some mouthguards include a mouthpiece and tether that connects the mouthpiece to a helmet while other mouthguards are untethered having only a mouthpiece free from any tether. The tether of the tethered mouthguards may assume a wide variety of strap sizes and styles.

The material of the mouthpiece is typically comprised of a plastic, or elastomer or some other substance that acts as a substrate supporting the growth of microorganisms. The growth of such microorganisms may cause hygienic and medical problems. While washing may alleviate or prevent these problems, athletes, whether young or old, routinely tend to wash their mouthguards less often than is desirable or necessary whether due to inconvenience, neglect or some other factor with microorganism buildup as the undesirable result.

UV radiant energy, a known antimicrobial sanitizer, has been employed in various devices to sanitize mouthguards and other objects such as toothbrushes that are subject to undesirable germ buildup as disclosed, for example, in US patent application publication US 2006/0242788 to Day, published Nov. 2, 2006; U.S. Pat. No. 6,461,568 to Eckhardt, issued Oct. 8, 2002; and Japanese Patent Document 9-225012, dated Sep. 2, 1997, to Kyoji. The heretofore known portable sanitizers employing antimicrobial UV radiant energy, however, have been disadvantageous in that they have not been able to sanitize both tethered and untethered mouthguards; have been subject to unintentional or unsafe UV actuation; and/or, among other things, have not been sufficiently robust to withstand the repeated use and the kind of heavy wear to which they typically are subjected from being carried about in athletic bags, thrown around in locker rooms or from other harsh or punishing treatment.

SUMMARY OF THE INVENTION

Accordingly, it is one object of the present invention to disclose a portable UV sanitizer for both tethered and untethered (free) mouthguards.

It is another object of the present invention to disclose a UV sanitizer for both tethered and untethered mouthguards that is not subject to unintentional or unsafe UV actuation.

It is another object of the present invention to disclose a UV sanitizer for both tethered and untethered mouthguards that is sufficiently robust to withstand repeated use and heavy wear.

It is a further object of the present invention to disclose a UV sanitizer for both tethered and untethered mouthguards that is able to accommodate tethers of a wide variety of strap sizes and styles.

Another object of the present invention is to disclose a UV sanitizer for both tethered and untethered mouthguards that is suitable for use with other dental products such as dental retainers and night-guards, tooth whitening trays, dentures, and the like mouth-related or other products.

A further object of the present invention is to disclose a UV sanitizer for both tethered and untethered mouthguards at least a portion of which is dishwasher safe.

Yet another object of the present invention is to disclose a UV sanitizer for both tethered and untethered mouthguards that is ergonomically shaped to both seat well in the hand and to be capable of being readily tossed and safely caught.

In accord with these and other objects, the present invention discloses a UV sanitizer for tethered and untethered mouthguards that includes a portable container defining a mouthpiece receiving cavity inside the portable container receiving mouthpieces of both tethered and free mouthguards and an antimicrobial UV light source interior to the mouthpiece receiving cavity for sanitizing the mouthpieces of both tethered and free mouthguards that may be received in the mouthpiece receiving cavity.

The portable container of the UV sanitizer for tethered and untethered mouthguards of the present invention includes first walls providing a mouth that inwardly opens to the mouthpiece receiving cavity and forms a tether receiving passageway through which an athletic mouthguard tether extends outwardly from said mouthpiece receiving cavity through said passageway when the mouthpiece of a tethered mouthguard is received in said mouthpiece receiving cavity.

Resiliently biased second walls are provided in said mouth which are operable to seal said mouth against UV light leakage when the mouthpiece of an untethered mouthguard is received in said cavity and operable to substantially seal both the confronting portion of the tether in the mouth extending out said passageway and any portion of said mouth not occupied by the tether when the mouthpiece of a tethered mouthguard is received in the mouthpiece receiving cavity and its tether outwardly extends through the passageway provided by said mouth.

The resiliently biased second walls preferably have open and normally biased closed positions. The resiliently biased second walls in normally biased closed position block UV light escaping out the mouth. The resiliently biased second walls are deflected from the normally biased closed position to assume an open condition in response to contact with a tether extending through the passageway of the mouth when a tethered mouthguard is received in the cavity.

In different presently preferred embodiments, the resiliently biased second walls having open and normally closed positions include a monolithic resilient tongue, a resilient toothed tongue, and resilient compressible lips. The resiliency of the resiliently biased second walls may be provided in ways other than by the resiliency of the material employed for the walls; for example, resilient second walls may be provided by a spring-loaded door mechanism or other means.

The portable container of the UV sanitizer for tethered and untethered mouthguards of the present invention preferably includes upper and lower jaw subassemblies. A hinge articulates the upper and lower jaws subassemblies for pivoting motion between open and closed conditions. The upper jaw subassembly preferably includes the antimicrobial UV lamp and associated circuitry, and the lower jaw subassembly provides a tray receiving the mouthpiece of athletic mouthguards.

The hinge subassembly pivotally articulating the upper and lower jaws subassemblies preferably is detachable allowing for dishwasher safe washing of the lower jaw subassembly. The open condition of the jaws grants access to said cavity and the closed condition permits the portable container to be used as a carrying or storage case.

Preferably, the upper and lower jaw subassemblies are shaped to present a convex outer aspect that corresponds to the concave surface of the inside of a hand such that the portable container with the upper and lower jaw assemblies in the closed condition seats well in the hand and may serve as a projectile that is able to be safely tossed and easily caught.

Preferably, plural switches are employed to prevent unintended actuation and to control safe UV actuation sequencing.

BRIEF DESCRIPTION OF THE DRAWINGS

These and other objects, inventive aspects and advantageous features of the presently disclosed invention will become apparent to those of skill in the art by having reference to the following, slowly exemplary, detailed description of the presently preferred embodiments, and to the drawings, wherein.

DETAILED DESCRIPTION OF THE PRESENTLY PREFERRED EMBODIMENTS

Referring now to FIGS. 1-10, generally designated at 10 is a UV sanitizer for tethered and untethered mouthguards in accord with the present invention. The UV sanitizer 10 includes lower and upper jaw subassemblies generally designated 12, 14 and a detachable hinge generally designated 16 that articulates the lower and upper jaw subassemblies 12, 14 for pivoting motion between open and closed conditions.

The lower jaw subassembly 12 defines a cavity generally designated 18 bounding a volume sufficiently large to receive the mouthpieces of tethered and untethered mouthguards. The inside bottom surface of the cavity 18 of the lower jaw subassembly 12 includes a reflective coating 20 and a pair of standoffs 22. The reflective coating 20 and standoffs 22 cooperate to expose to UV antimicrobial radiant energy the undersides of the mouthpieces of tethered or untethered mouthguards when received in the cavity 18 during UV actuation. Resilient seals, not shown, may be provided about one or both of the confronting peripheral edges of the upper and lower jaw subassemblies 12, 14. The resilient seals prevent UV light leaking out the cavity 18 and also provide a measure of mechanical energy absorption that improves impact resistance and enhances robustness and durability.

Figure 6:
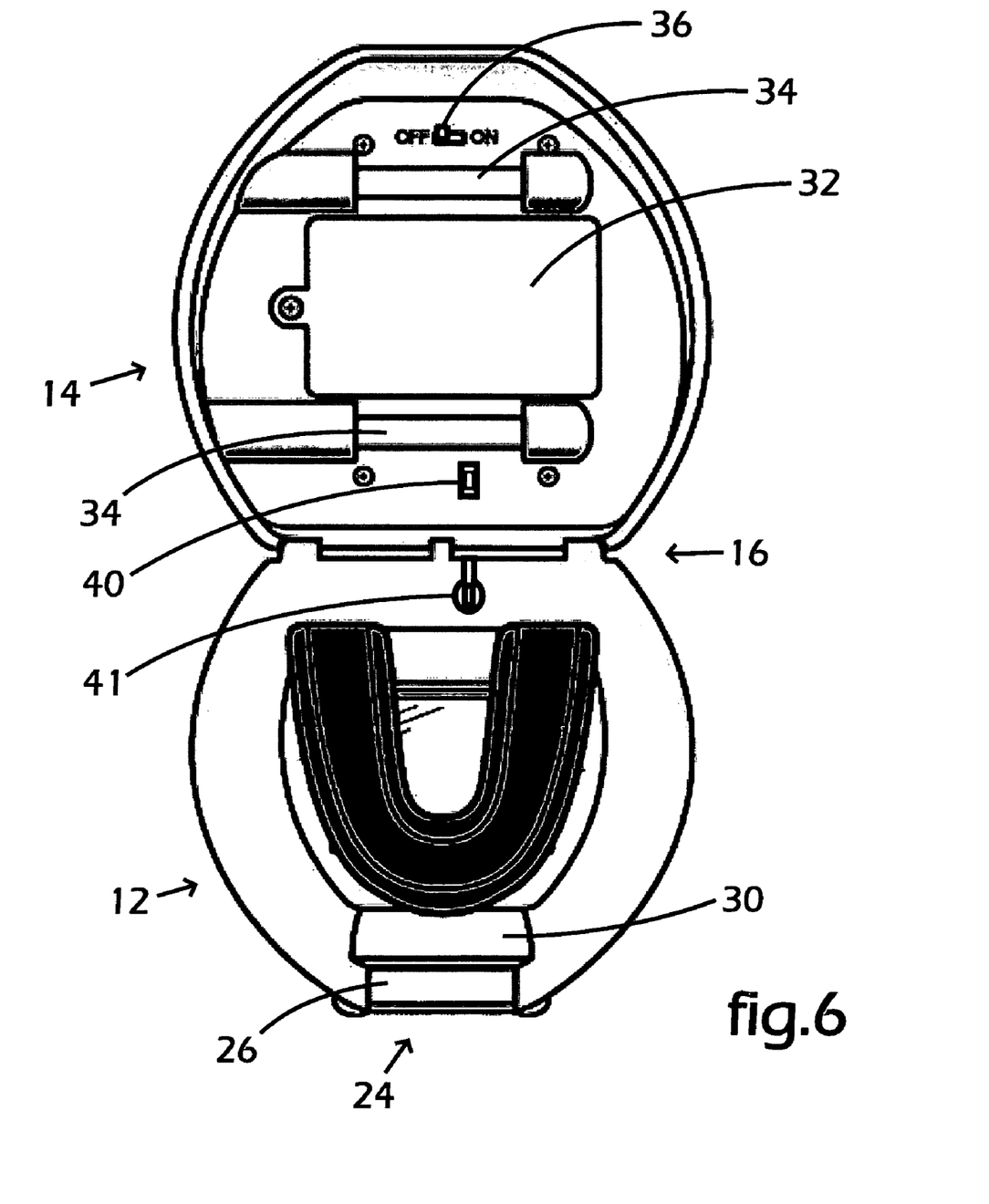
FIG. 6 is a top pictorial view of a UV sanitizer for tethered and untethered mouthguards in accord with the present invention in an open condition showing an untethered, or free, mouthguard received in the tray of the bottom jaw subassembly.
Figure 7:
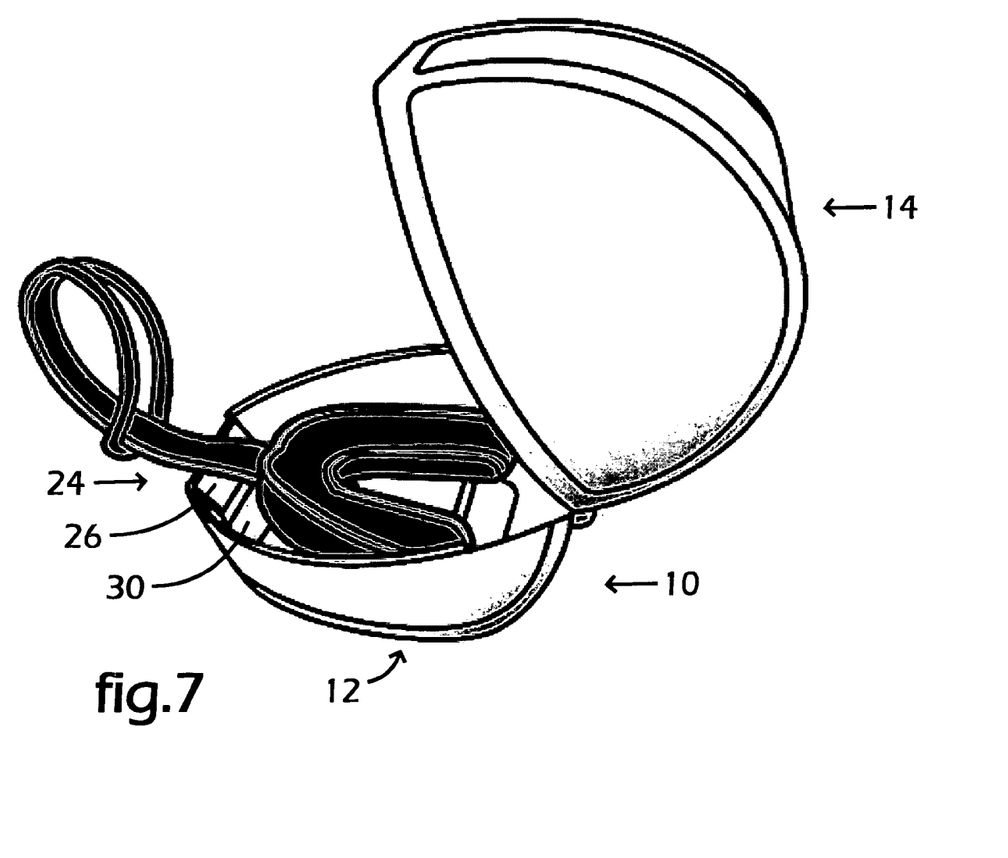
FIG. 7 is a top and side pictorial view showing a tethered mouthguard received in the tray of the bottom jaw subassembly of a UV sanitizer for tethered and untethered mouthguards in accord with the present invention in an open condition.
Figure 8:
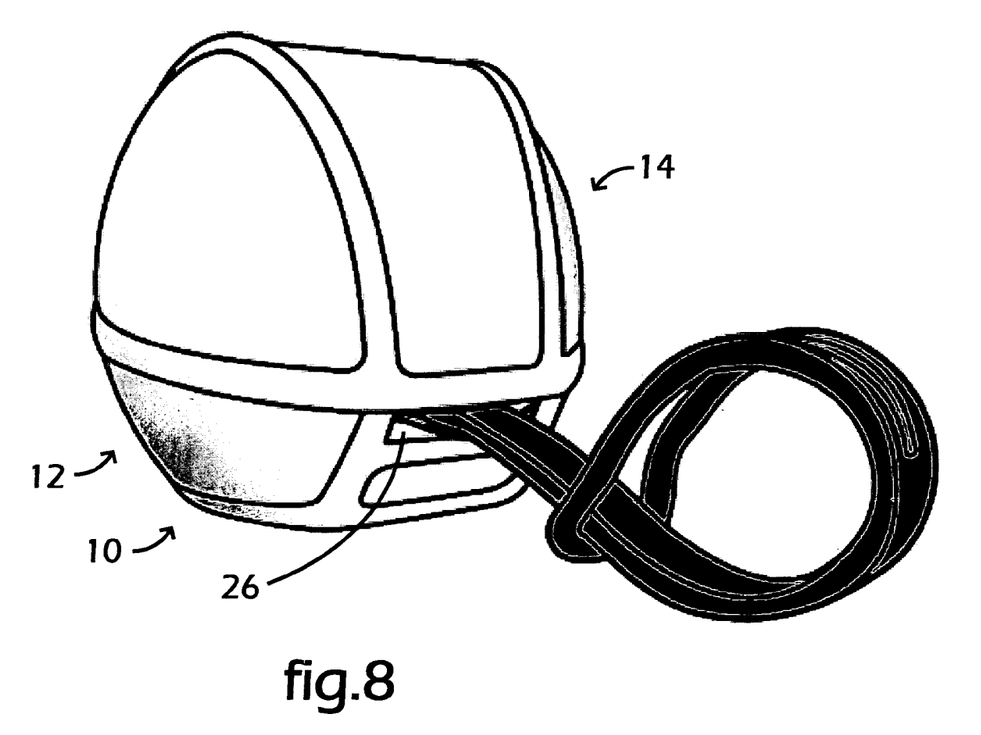
FIG. 8 is a side and front pictorial view of a UV sanitizer for tethered and untethered mouthguards in accord with the present invention in its closed condition showing an extending tether of a tethered mouthguard received therein.

The lower jaw subassembly 12 includes a mouth generally designated 24 in open communication with the cavity 18 that defines a passageway accommodating a tether whenever the mouthpiece of a tethered mouthguard is received in the cavity 18. A resilient tongue 26 is attached to the lower jaw subassembly 12 by posts 28 and retaining plate 30 that closes the mouth 24. The resilient tongue 26 has open and normally biased closed positions. The resilient tongue 26 closes the mouth 24 in its normally biased closed condition while it is deflected to its open condition in response to contact with a tether. The resilient tongue 26 is operative in its normally biased closed condition to seal the mouth 24 whenever the cavity 18 is empty or the mouthpiece of a free mouthguard is received in the cavity 18, as shown in FIG. 6, and is operative to assume an open position in response to being bent by contact with the tether in such a way as to substantially seal the confronting surface of a tether extending through the mouth against UV light leakage, and to substantially seal, by the tongue's inherent resilient restoring action, any portion of the mouth that is not occupied by the tether, whenever the mouthpiece of a tethered mouthguard is received in the cavity 18, as shown in FIGS. 7, 8.

The resilient tongue 26 cooperates with the mouth 24 to accommodate a wide variety of tethers of different cross-sectional sizes and shapes. The resilient tongue 26 is preferably fashioned of silicon material. Although silicon is preferred as the material of the tongue 26, any resilient material soft enough not to impede the tether but firm enough to provide a light sealing action against the tether and a sealing action in any portion of the mouth not occupied by the tether may be employed.

Figure 1:
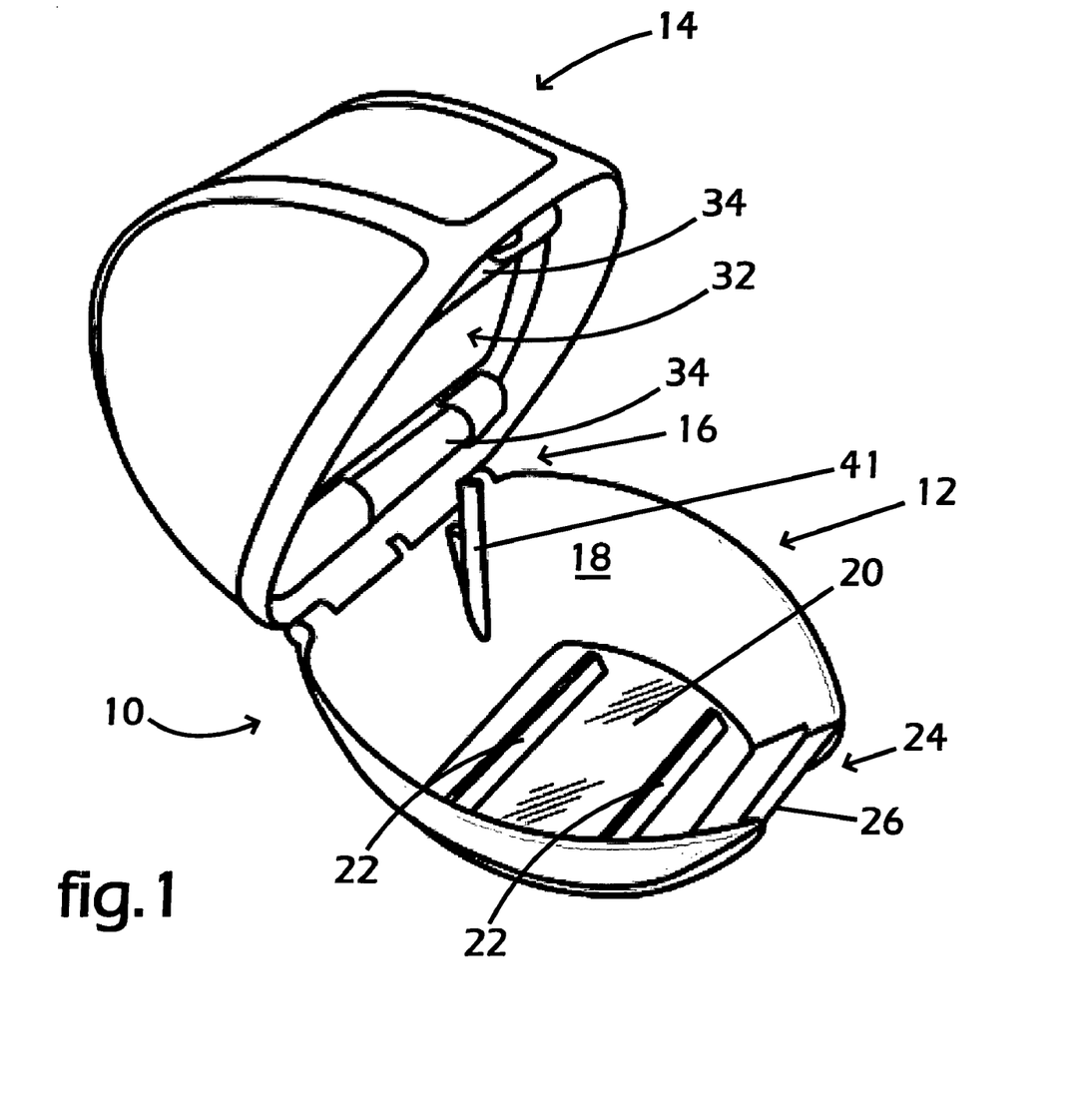
FIG. 1 is a side and top pictorial view of a UV sanitizer for tethered and untethered mouthguards in accord with the present invention showing it in an open condition.
Figure 2:
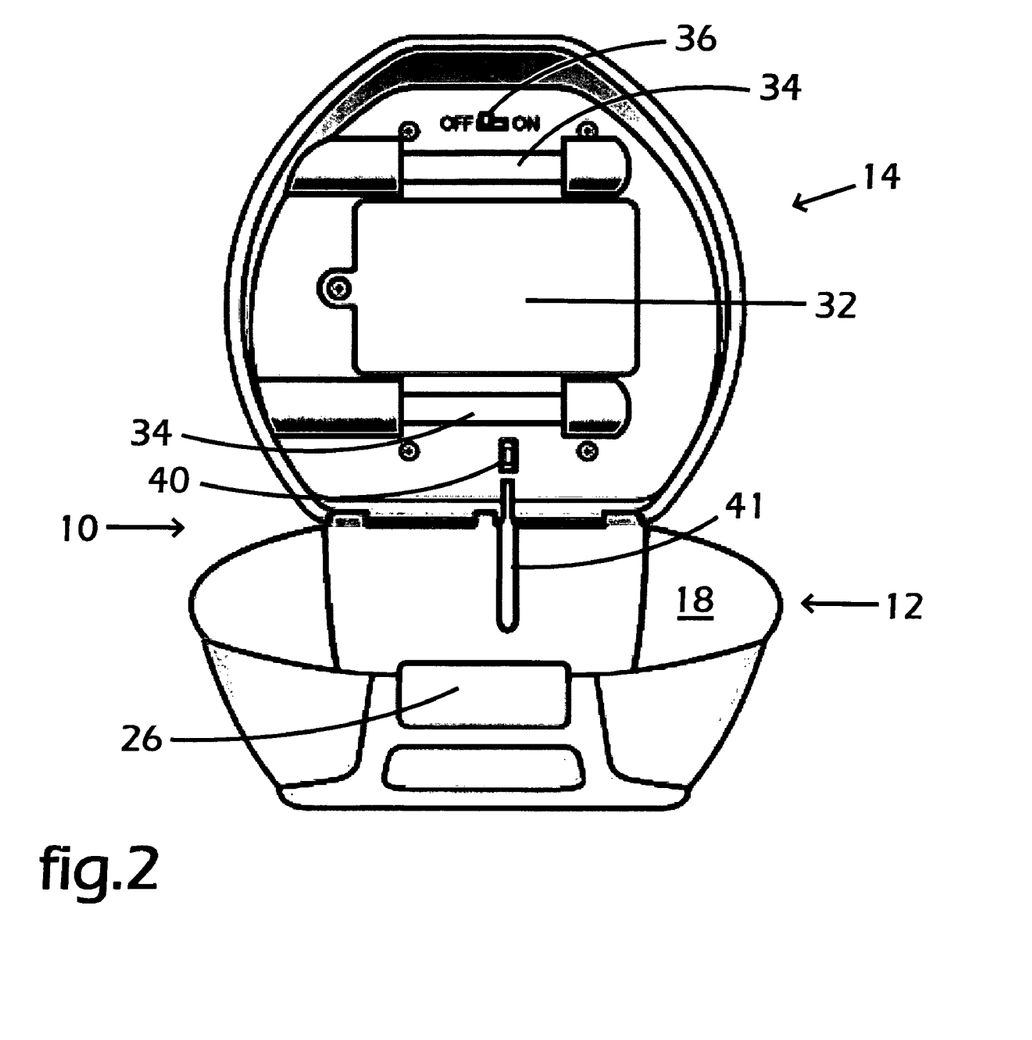
FIG. 2 is a front pictorial view of the same.
Figure 3:
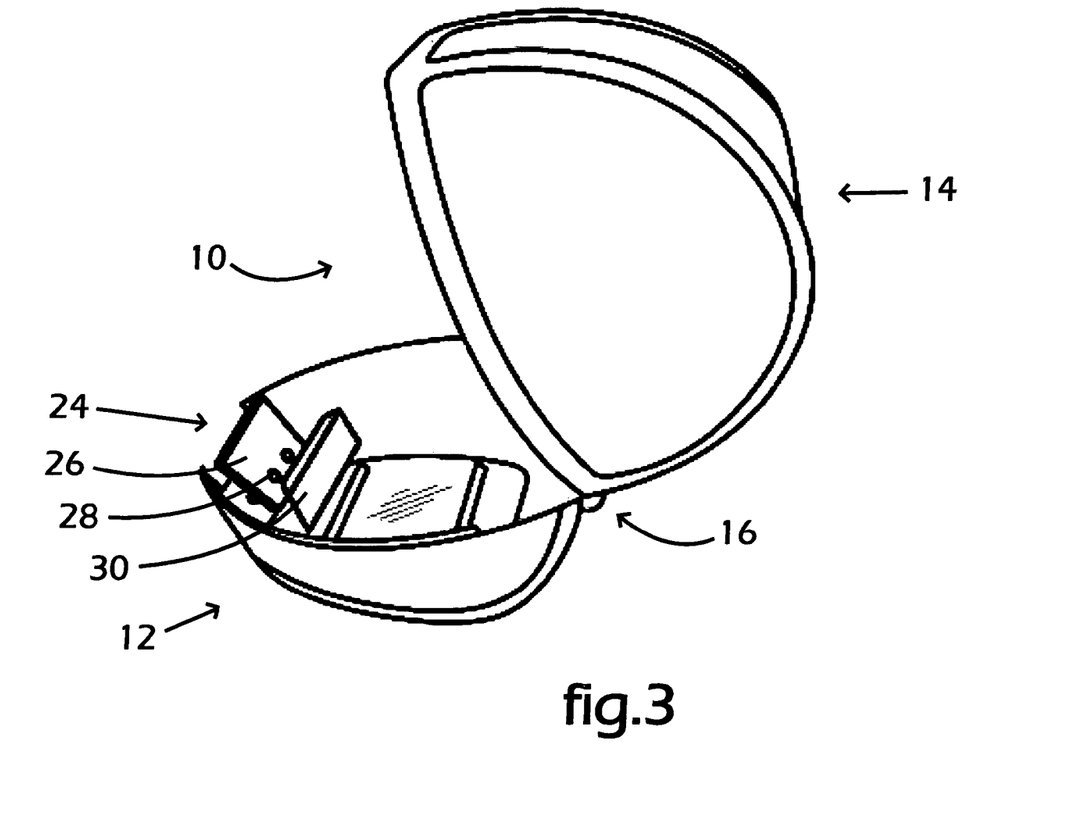
FIG. 3 is a front and side exploded pictorial view of one monolithic resilient tongue embodiment of a UV sanitizer for tethered and untethered mouthguards in accord with the present invention.
Figure 4:
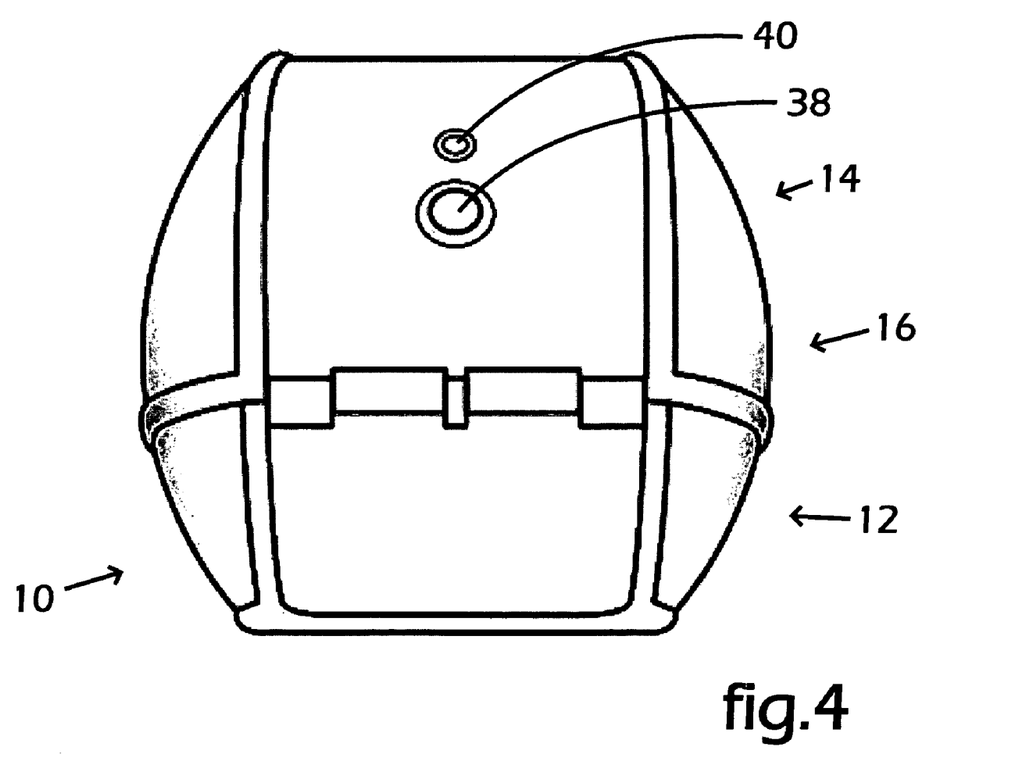
FIG. 4 is a pictorial view of the back of a UV sanitizer for tethered and untethered mouthguards in accord with the present invention in its closed condition.

The upper jaw subassembly 14 includes a battery compartment generally designated 32, UV lamps 34 and a printed circuit board, not shown, that includes a timer circuit and a UV lamp driver circuit to be described. An inside control switch 36, as seen in FIGS. 2, 6, and an outside control switch 38, as shown in FIG. 4, are provided on the upper jaw subassembly 14. An outside "power on" LED preferably is provided on the upper jaw subassembly 14. A recessed safety switch 40 and cooperative finger 41 are respectively provided on the upper jaw subassembly 14 and the lower jaw subassembly 12, as shown in FIGS. 2, 6.

Figure 5:
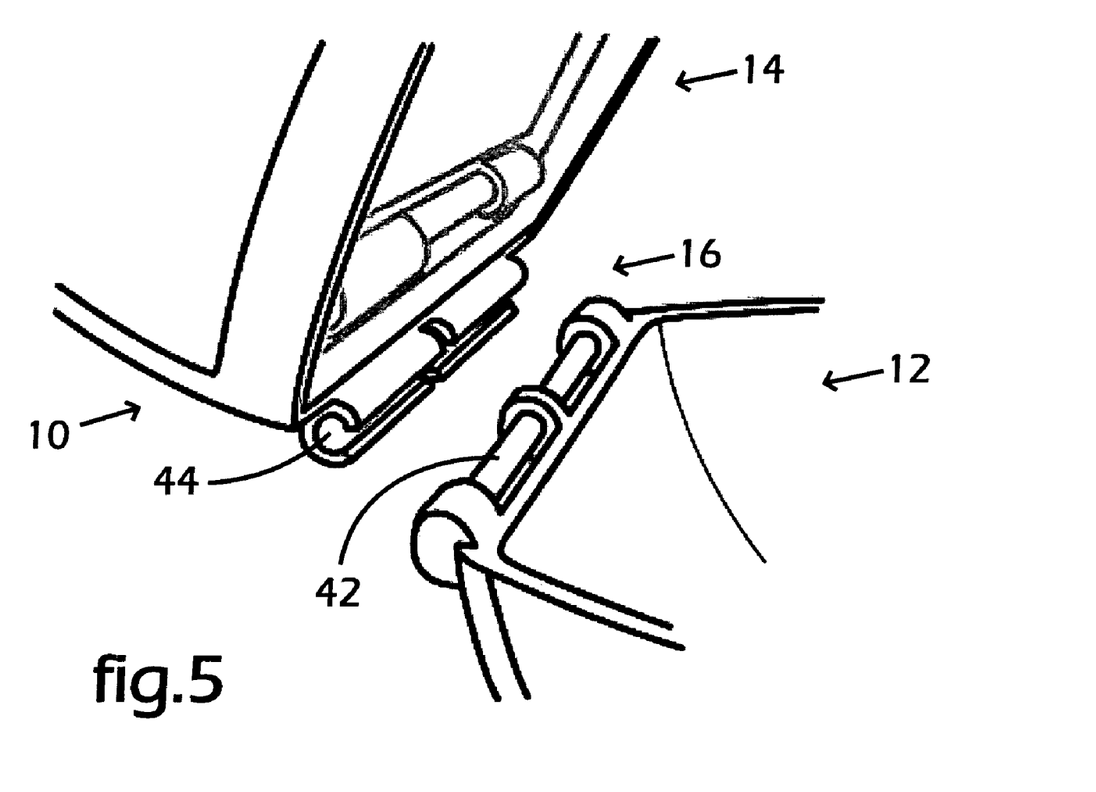
FIG. 5 is an exploded side pictorial detail view showing the detachable hinge pivotally articulating the upper and lower jaw subassemblies of a UV sanitizer for tethered and untethered mouthguards in accord with the present invention.

The lower jaw subassembly 12 may be periodically detached from the upper jaw subassembly 14 for washing. The hinge 16 includes shaft 42, carried by the lower jaw subassembly 12, and slotted bearings 44, carried by the upper jaw subassembly 16, by means of which the upper and lower jaw subassemblies 12, 14 are detachable. Although a snap-fit detachable hinge is presently preferred, any detachable pivot hinge or other articulation may be employed.

Figure 9:
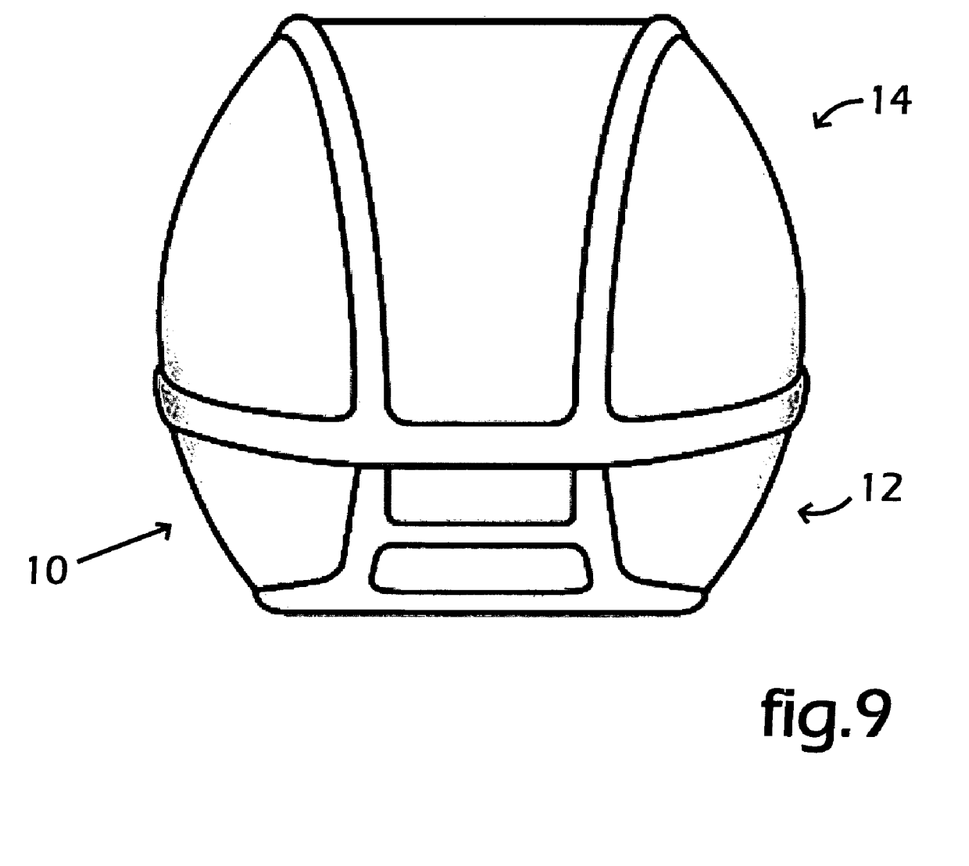
FIG. 9 is a front side pictorial view of a UV sanitizer for tethered and untethered mouthguards in accord with the present invention in its closed condition.
Figure 10:
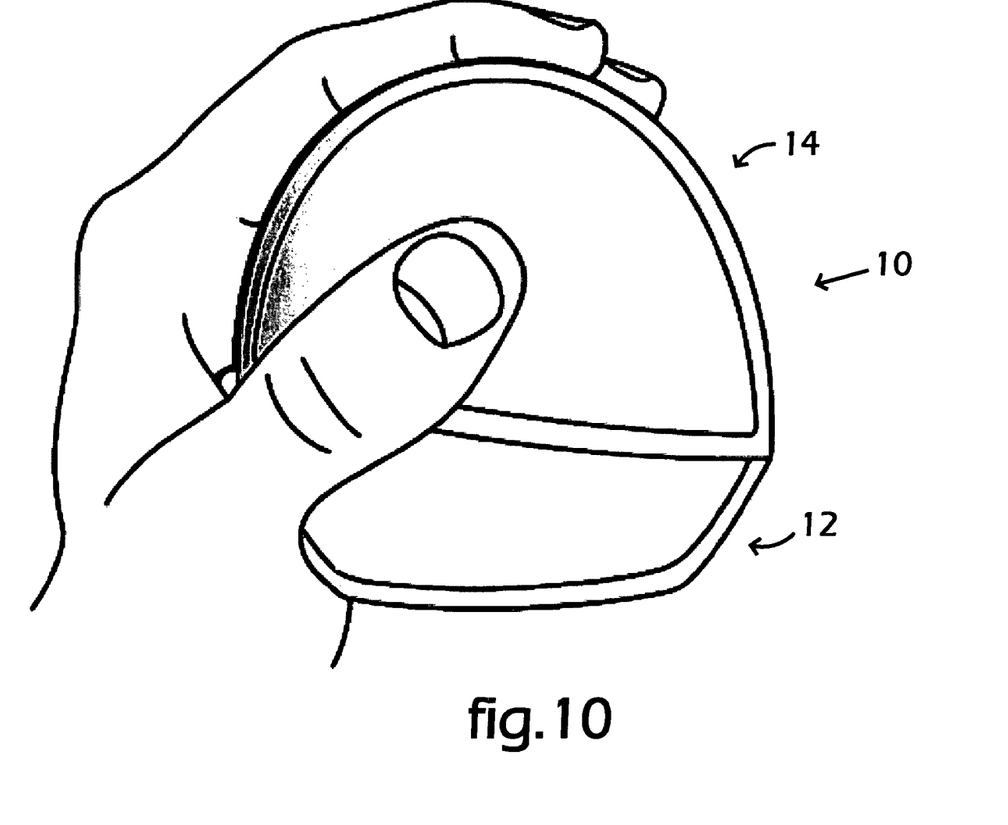
FIG. 10 is a side pictorial view of a UV sanitizer for tethered and untethered mouthguards in accord with the present invention illustrating its econometric design for easy gripping in the hand and which allows it to be readily tossed and securely caught.

As shown in FIGS. 9, 10, the upper and lower jaw subassemblies 12, 14 have a convex outside surface. The convex outside surface cooperates with the naturally concave curvature of the hand allowing the UV sanitizer 10 to be palmed and/or tossed and caught. The capacity to be palmed and/or tossed and caught, whether used or not for this purpose, is believed to make the UV sanitizer for tethered and untethered mouthguards of the present invention more attractive to have and use and thereby is believed to synergistically enhance its utility. The convex outside surface also provides a measure of impact resistance if dropped. The arcuate exterior surface of the UV sanitizer may be patterned to present surface features when molded, and/or painted, or otherwise fashioned to emulate a sports ball, such as a baseball, soccer ball and so forth. The sports ball emulation is believed to make the UV sanitizer for tethered and untethered mouthguards of the present invention more attractive to have and use and thereby is believed to synergistically enhance it utility.

Figure 11:
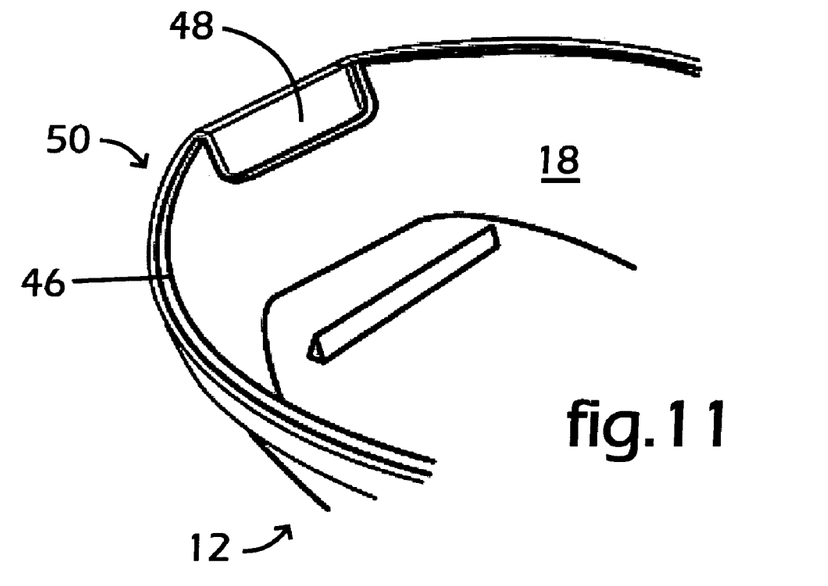
FIG. 11 is a pictorial view of the lower jaw subassembly illustrating another embodiment of a monolithic resilient tongue of a UV sanitizer for tethered and untethered mouthguards in accord with the present invention.

An alternate embodiment of a monolithic resilient tongue is shown in FIG. 11. A peripheral edge seal 46 includes a monolithic resilient tongue 48 integral with edge seal 46 that seats in the mouth generally designated 50 in communication with the cavity 18 of the lower jaw subassembly 12. The peripheral seal 46 is adhesively joined to the confronting edge of the lower jaw body 12 about its top periphery and along the edges of the walls providing the mouth 50. The monolithic resilient tongue 48 is fashioned of the same material and operates in substantially the same way as the monolithic tongue 26 described above in connection with the description of the FIGS. 1-10 embodiment thereof and its operation is not further described herein for the sake of brevity of explication.

Figure 12:
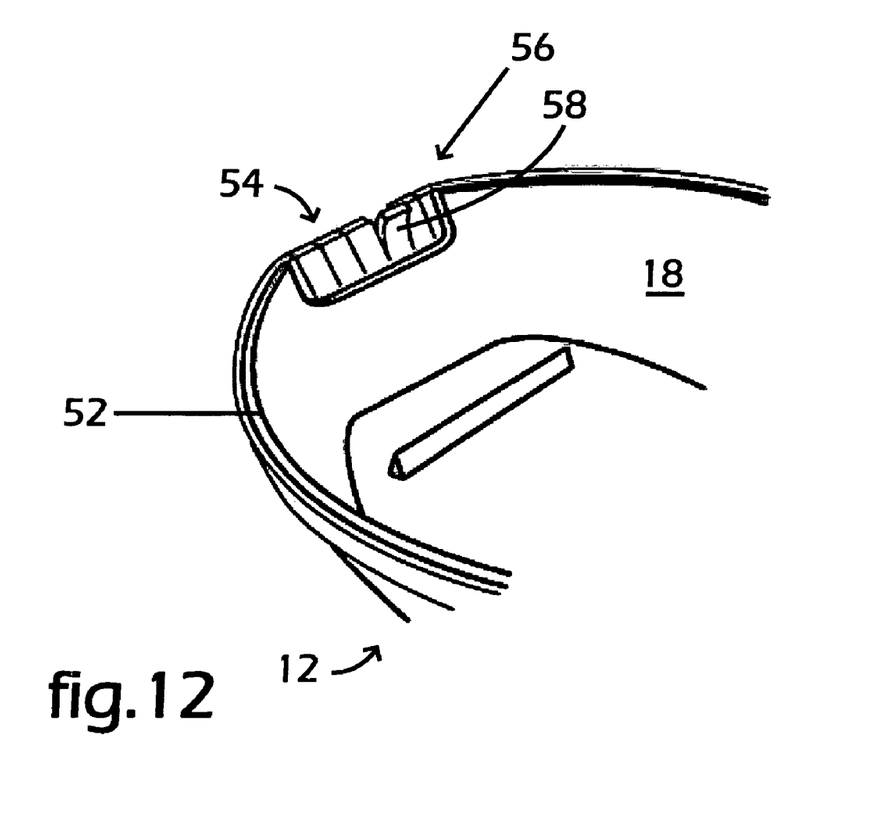
FIG. 12 is a pictorial view of the lower jaw subassembly illustrating another resilient, toothed tongue embodiment of a UV sanitizer for tethered and untethered mouthguards in accord with the present invention.

An alternate embodiment of a toothed resilient tongue is shown in FIG. 12. A peripheral edge seal 52 includes a toothed resilient tongue generally designated 54 that seats in the mouth generally designated 56 in communication with the cavity 18 of the lower jaw subassembly 12. The tongue 54 is preferably of the same material as the other tongues described herein. The peripheral seal 52 is adhesively joined to the confronting edge of the lower jaw body 12 about its top periphery and along the edges of the walls providing the mouth 56.

The tethers of tethered mouthguards come in a variety of sizes and styles from a round string to molded plastic tether pieces having round, flat, or other cross-section. The number and width of each tooth 58 of the toothed tongue 54 determine which and how many are bent in response to contact with a tether of given size and style. As will be appreciated, for any given number and width, the resilient toothed tongue 54 is, as are the other herein disclosed embodiments thereof, capable of accommodating a wide variety of tether sizes and styles.

Figure 13:
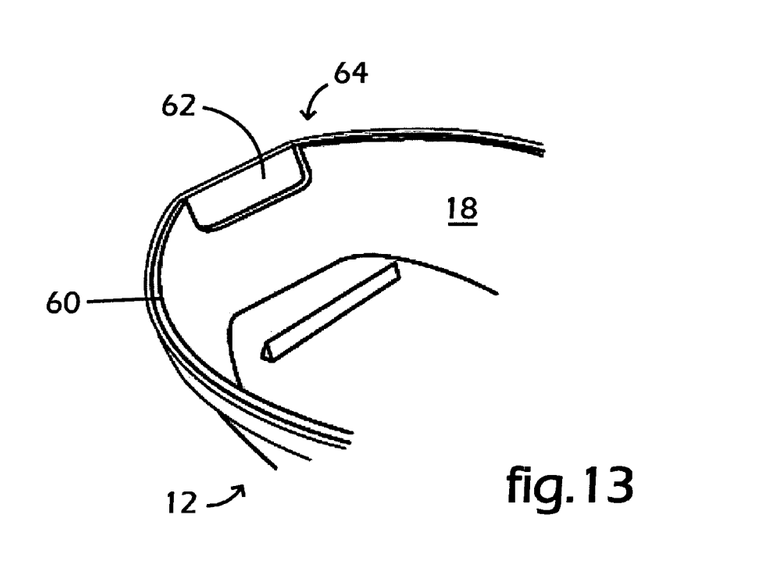
FIG. 13 is a pictorial view of the lower jaw subassembly illustrating another resilient, compressible lip embodiment of a UV sanitizer for tethered and untethered mouthguards in accord with the present invention.

An alternate embodiment of a resilient compressible lip is shown in FIG. 13. A peripheral edge seal 60 includes a resilient compressible lip 62 that seats in the mouth generally designated 64 in communication with the cavity 18 of the lower jaw subassembly 12. The resilient lip 62 is preferably of the same material as the herein described tongue embodiments. The peripheral seal 60 is adhesively joined to the confronting edge of the lower jaw body 12 about its top periphery and along the edges of the walls providing the mouth 64. The resilient compressible lip 62 is deflected by contact with a tether to seal the tether's confronting surface when the mouthpiece of a tethered mouthguard is received in the cavity 18 and it assumes its normally biased closed position to seal the mouth 64 when the mouthpiece of an untethered mouthguard is received in the cavity, or when the cavity is empty.

The resilient tongues and lips may be variously embodied; for example, they may be entirely carried by either of the upper and lower jaw subassemblies or one part thereof may be carried by the lower jaw subassembly and the complementary parts thereof may be carried by the upper jaw subassembly.

Figure 14:
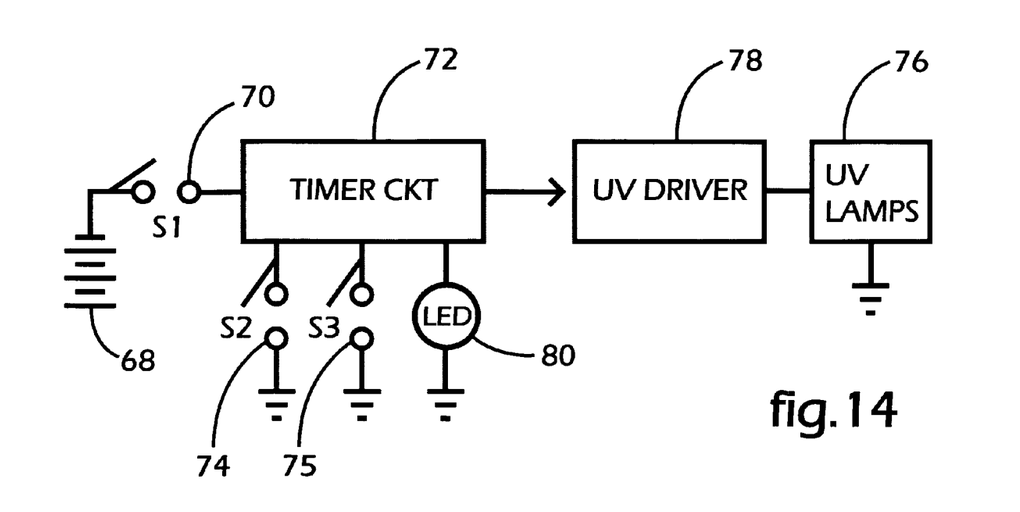
FIG. 14 is an electrical block diagram of a UV sanitizer for tethered and untethered mouthguards in accord with the present invention.

Referring now to FIG. 14, generally designated at 66 is an electrical block diagram of a UV sanitizer for tethered and untethered mouthguards in accord with the present invention. A battery 68 is connected via master power switch 70 to a timer circuit 72. Designated "S1," the master power switch 70 as described above preferably is mounted to the outside of the sanitizer's portable housing. Designated "S2," a second switch 74 preferably mounted as described above inside the cavity is connected to the timer circuit 72. Designated "S3," a third "safety" switch 75 preferably mounted as described above recessed in the upper jaw subassembly is operatively connected to the timer circuit 72. Antimicrobial UV radiant source(s) 76 are connected to the timer circuit 72 via UV lamp driver circuit 78. In the preferred embodiment the timer circuit 72 initiates a ten (10) minute cycle and then turns the radiant source(s) 76 "off." During UV actuation, power on LED 80, operatively connected to timer circuit 72, is lighted. Although exposure of the mouthpieces of tethered or untethered mouthguards to UV radiant energy for ten (10) minutes duration is presently preferred, it will be appreciated that any intensity and duration of antimicrobially effective UV radiant energy may be employed. The switches 70, 74, 75, which must be "on," cooperate to prevent unintended actuation and to safely initiate antimicrobial UV actuation sequencing. The safety switch 75 only engages when the portable container is in closed condition. Once a timer cycle is started, if the portable container is opened at any time, the switch 75 becomes disengaged and the UV lamp(s) are shut off. This prevents any chance of someone running the UV lamps should the container be open and thus prevents any possible direct UV light exposure to user's eyes. If the container is opened during a cycle, the UV lamp(s) are shut "off" and the timer automatically resets. Once re-started, a full timer cycle is presently preferred.

Many modifications of the presently disclosed invention will become apparent to those of skill in the art having benefitted by instant disclosure without departing from the inventive concepts.

What is claimed is:

1. A UV sanitizer for tethered and untethered mouthguards, comprising:

a portable container defining a mouthpiece receiving cavity inside the portable container receiving mouthpieces of both tethered and free mouthguards and an antimicrobial UV light source interior to the mouthpiece receiving cavity for sanitizing the mouthpieces of both tethered and free mouthguards that may be received in the mouthpiece receiving cavity;

said portable container having first walls providing a mouth that inwardly opens to the mouthpiece receiving cavity and forms a tether receiving passageway through which a tether of an athletic mouthguard may extend out said mouth of said cavity when the mouthpiece of a tethered mouthguard is received in the mouthpiece receiving cavity;

said portable container having resiliently biased second walls in said mouth which are operable to seal said mouth against UV light leakage when the mouthpiece of an untethered mouthguard is received in said cavity and operable to substantially seal both the confronting portion of the tether in the mouth extending out said passageway and any portion of said mouth not occupied by the tether when the mouthpiece of a tethered mouthguard is received in the mouthpiece receiving cavity and its tether outwardly extends through the passageway provided by said mouth.

2. The invention of claim 1, wherein the resiliently biased second walls have open and normally biased closed positions, wherein said resiliently biased second walls in said normally biased closed position block UV light escaping out said mouth whenever the mouthpiece of an untethered mouthguard is received in said cavity and wherein said resiliently biased second walls are deflected to said open condition in response to contact with a tether extending through said passageway of said mouth when the mouthpiece of a tethered mouthguard is received in said cavity.

3. The invention of claim 1, wherein the resiliently biased second walls include a monolithic resilient tongue.

4. The invention of claim 3, wherein said monolithic resilient tongue is attached to said portable container by mounting hardware.

5. The invention of claim 3, wherein said monolithic resilient tongue is adhesively attached to said portable container.

6. The invention of claim 1, wherein the resiliently biased second walls include a toothed resilient tongue.

7. The invention of claim 6, wherein said toothed resilient tongue is adhesively attached to said portable container.

8. The invention of claim 1, wherein the resiliently biased second walls include at least one resilient compressible lip.

9. The invention of claim 8, wherein said at least one resilient compressible lip is adhesively attached to said portable container.

10. The invention of claim 1, wherein said portable container includes upper and lower jaw subassemblies articulated for motion between open and closed conditions.

11. The invention of claim 10, further including a hinge articulating the upper and lower jaws subassemblies for pivoting motion between said open and closed conditions.

12. The invention of claim 10, wherein said upper jaw subassembly includes the antimicrobial UV lamp and associated circuitry operatively connected to the antimicrobial UV lamp to controllably energize the same, and the lower jaw subassembly provides a tray receiving the mouthpiece of athletic mouthguards.

13. The invention of claim 12, wherein the hinge subassembly pivotally articulating the upper and lower jaws subassemblies is detachable allowing dishwasher safe washing of the lower jaw subassembly.

14. The invention of claim 12, wherein said tray includes a reflective coating.

15. The invention of claim 12, wherein said tray includes standoffs.

16. The invention of claim 10, wherein the upper and lower jaw subassemblies are shaped to present a convex outer aspect that corresponds to the concave surface of the inside of a hand such that the upper and lower jaw assemblies in their closed condition seats well in the hand and is able to be readily tossed and safely caught.

17. The invention of claim 16, wherein the convex outer aspects of the upper and lower jaws subassemblies are patterned to emulate the standardized appearance of a particular sports ball.

18. The invention of claim 10, wherein dual switches, one mounted externally and the other mounted interior to the portable container, are cooperative to prevent unintended actuation of the UV light source and to initiate safe UV actuation sequencing.

19. The invention of claim 18, further including a safety switch recessed within one jaw and an actuating finger mounted to the other jaw responsive to said portable container being in an open condition to interrupt UV illumination to prevent direct UV viewing.

* * * * *